United States Patent
Bruning et al.

(10) Patent No.: US 9,084,810 B2
(45) Date of Patent: Jul. 21, 2015

(54) METHODS AND COMPOSITIONS FOR ENHANCING HAIR QUALITY USING BLACKBERRY EXTRACT

(71) Applicant: Johnson & Johnson Consumer Companies, Inc., Skillman, NJ (US)

(72) Inventors: Elizabeth Bruning, Somerset, NJ (US); Euen Thomas Graham Ekman Gunn, Hopewell, NJ (US); Frank Liebel, Point Pleasant, NJ (US); Samantha Tucker-Samaras, Long Valley, NJ (US); Dina VanWyck, Toms River, NJ (US); Delores Santora, Ringoes, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 14/510,520

(22) Filed: Oct. 9, 2014

(65) Prior Publication Data
US 2015/0024076 A1    Jan. 22, 2015

Related U.S. Application Data

(62) Division of application No. 13/765,498, filed on Feb. 12, 2013, now Pat. No. 8,962,041.

(51) Int. Cl.
| | | |
|---|---|---|
| *A01N 65/00* | (2009.01) | |
| *A61K 36/73* | (2006.01) | |
| *A61K 45/06* | (2006.01) | |
| *A61K 36/45* | (2006.01) | |
| *A61K 36/00* | (2006.01) | |
| *A61Q 7/00* | (2006.01) | |
| *A61K 8/97* | (2006.01) | |

(52) U.S. Cl.
CPC . *A61K 36/73* (2013.01); *A61K 8/97* (2013.01); *A61K 36/00* (2013.01); *A61K 36/45* (2013.01); *A61K 45/06* (2013.01); *A61Q 7/00* (2013.01)

(58) Field of Classification Search
CPC ............................ A61K 36/45; A61K 36/00
USPC ..................................................... 424/725
See application file for complete search history.

(56) References Cited

FOREIGN PATENT DOCUMENTS

| | | |
|---|---|---|
| DE | 2255341 A1 | 5/1974 |
| FR | 2951943 A1 | 5/2011 |
| JP | 2004091390 A | 3/2004 |
| WO | WO 2005/123101 A1 | 12/2005 |
| WO | WO 2011/078832 A1 | 6/2011 |
| WO | WO 2011/102813 A2 | 8/2011 |

OTHER PUBLICATIONS

Sung Y.K. et al.; "the hair growth promoting effect of ascorbic acid 2-phosphate, a long-acting Vitamin C derivative"; Journal of Dermatological Science, Elsevier Science Publishers , Shannon, IE, vol. 41, No. 2 Feb. 1, 2006 pp. 150-152.
Anonymous: "GNPD—Regenerative Hair Mask"; May 1, 2010.
Danaher R J et al. "Antiviral Effects of Blackberry Extract Against Herpes Simplex Virus Type 1". Oral Surgery, Oral Medicine Oran Pathology, Oral Radiology and Endodontology, vol. 112, No. 3, E31-E35, 2011.
Elisia I. "The Protective Effect of Blackberry Anthocyanins against Free Radical-Induced Oxidation and cytotoxicity in Multiple Cell Lines" Thesis submitted at the University of British Columbia, 2005.

*Primary Examiner* — Michael Meller

(57) ABSTRACT

Compositions and methods for inducing hair growth and improving hair quality utilizing extracts of blackberry in an amount effective to induce hair growth when applied topically to an area of the skin on which hair growth is desired.

3 Claims, No Drawings

METHODS AND COMPOSITIONS FOR ENHANCING HAIR QUALITY USING BLACKBERRY EXTRACT

CROSS-REFERENCE TO RELATED APPLICATION

The present application is a divisional application claiming the benefit of the earlier filing date of U.S. patent application Ser. No. 13/765,498, filed Feb. 12, 2013, the entirety of which application is hereby incorporated by reference herein as if fully set forth herein.

FIELD OF THE INVENTION

This invention relates to topical compositions and methods for inducing hair growth and improving hair quality utilizing extracts from the Blackberry plant (*Rubus fruticosus*).

BACKGROUND OF THE INVENTION

Genetic disposition as well as the natural aging process and/or disease contribute to hair loss and slower hair growth in both males and females. Approximately 50% of the population displays this trait to some degree by the age of 50, and thinning of the hair can begin between 12 and 40 years of age independent of gender. Thus, agents able to stimulate hair growth as well as prevent and slow down or reduce hair loss could be beneficial not only to cure alopecia but to affect positively the psychosocial events associated with hair disorders. Studies reveal psychosocial impact with hair loss to include body image dissatisfaction associated with negative stereotypes, such as feeling older, weaker and less attractive.

Drugs, including Minoxidil (Rogaine), Finasteride (Propecia) and Dutasteride (Avodart) are approved treatments for hair loss. However, they may require medical prescription, and are active only on a certain percent of the population. Moreover, some of these drugs are not permitted to be used by females due to hormonal effects. For example, premenopausal women should not take Finesteride due to the risk of male pseudo-hermaphroditism to the fetus. Finasteride has been found to lower artificially the results of the prostate-specific antigen (PSA) test, the standard screening test for prostate cancer which can delay the detection and the treatment of the disease.

Minoxidil is a topically applied drug that is effective in inducing hair growth for a subset of patients and will re-grow hair only on top of the scalp. Further, it has limited effect on older people. Minoxidil may slow the rate of hair loss in five out of ten male patients.

Other medical treatments available to treat hair loss include drastic surgical techniques such as scalp reduction, scalp flaps or follicular unit transplantation. These surgeries carry the risk of complications such as elevation of hairline associated with donor region, possibility of necrosis and unnatural appearance of hair growth direction, anesthesia and post-op care, not to mention high costs.

Herbal preparations that claim to induce hair growth (e.g. Hair Prime) are available at low cost but their effectiveness is very limited.

M. Herrmann et al. have described that a hydroalcoholic blackberry leaf extract (SymMatrix), exhibits the MMP-1, MMP-2, and MMP-9 inhibitory activity. (See, for example, US2008/0095719

SUMMARY OF THE INVENTION

Surprisingly, we have found that a concentrated, aqueous *Rubus fruticosus* extract can effectively induce hair growth by applying a composition comprising, consisting essentially and consisting of such extract to the scalp, the skin, the eyelashes, eyebrows, mustache region or beard region of a patient a topically active composition comprising a concentration of at least 90 mg extract/ml of solution but less than 300 mg/ml of a *Rubus fruticosus* extract, which may start to increase hair coverage to the area of interest after daily application for at least five (5) to seven (7) days. We observed a potent increase in hair growth in vivo in all animals treated with a concentrated *Rubus fruticosus* extract. Even more surprisingly, the compositions of our invention containing *Rubus fruticosus* extract initially induced a visible telogen phase (i.e., shedding of club hairs) prior to rapid entry into the anagen phase (i.e., active growth phase of hair follicles). The compositions of our invention induced anagen in 100% of animals treated over a period of at least eight days.

DETAILED DESCRIPTION OF THE PREFERRED EMBODIMENTS

As used herein, "blackberry extract" means the extract of a plant of the genus *Rubus*. Preferably, the species utilized in the compositions of this invention is *Rubus fruticosus*. Blackberry extract may be a blend of compounds isolated from the plant of the genus *Rubus*. In one embodiment, the compounds are isolated from the flowers of the plant. In another embodiment, the compounds may be isolated from dried flowers of the plant. They may also be isolated from one or more parts of the plant, including the whole plant, flower, seed, root, rhizome, stem, fruit and/or leaf of the plant. Preferably, blackberry extract useful in the compositions of this invention is isolated from the leaf of the blackberry plant.

The extraction process may include physically removing a piece of the blackberry plant and grinding it. Organic solvent extraction processes known to those of skill in the art may also be used to obtain the blackberry extracts useful in the compositions of this invention. Solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide may be used to extract active compounds from the blackberry plant.

A blackberry leaf extract may also be prepared by an extraction produced with water, using alcohols such as ethanol or combination thereof as the extractant. However, an extract produced with an extractant including both ethanol and water extractant.

Blackberry leaves are preferably dried prior to extraction. It is also preferable to use only the leaves of the blackberry plant for the extraction and not also other plant parts such as the fruit (berries) of the blackberry, its branches, flowers or roots.

In one embodiment, the process of the extraction for the production of a blackberry leaf extract may have the following steps: a) addition to blackberry leaves of an extractant containing an alcohol selected from the group consisting of methanol, ethanol, n-propanol, isopropanol, and b) extraction of the blackberry leaves with the extractant for up to 72 hours.

The ratio of the mass of extractant to leaf solids is preferably established such that at least a 10-fold mass of extractant relative to the leaf solids and preferably no more than a 50-fold mass of extractant relative to the leaf solids is obtained, preferably a 10-to 20-fold mass. A 14-to 18-fold mass of extractant relative to the leaf solids is particularly preferably used for extraction. Good results were achieved with a 16-fold mass of an ethanol-containing solvent (relative once again to the leaf solids).

The extraction time for performing step (b) is at most 72 hours but can also be shorter. With particularly short extraction times, a relatively dilute extract is obtained in step (b). It is therefore preferable to extract the blackberry leaves in step (b) for at least one (1) hour, and more preferably, for at least two (2) hours. The preferred extraction time is chosen on the basis of the quality of the blackberry leaves to be extracted, particularly their age of the leaves and of the other extraction conditions, particularly the extraction temperature.

At elevated extraction temperatures, for example, at an extraction temperature in the range from about 60 to about 100° C., preferably in the range from about 80 to about 100° C., the extraction time is preferably about one hour to about six hours and more preferably about two to about four hours.

In addition, it is most preferable to perform the extraction in step (b) by refluxing the extractant, particularly at extraction temperatures in the range from about 60° C. to about 100° C., and more preferably in the range from about 80 to about 100° C. When using the refluxing process, the extraction time is preferably no more than about 24 hours.

The extraction temperature is established on the basis of the extractant that is used. If an ethanol-containing solvent is used, an extraction temperature in the range from about 60° C. to about 100° C., in particular an extraction temperature in the range from about 80° C. to about 100° C., is preferred, particularly if a mixture of ethanol and water is used as the extractant.

Preferably, the extractant contains a lower alkyl alcohol solvent, more preferably ethanol, in a proportion of at least about 20 wt. %, relative to the total extractant. Preferably, the extractant should also contain water in a proportion of at least 15 wt. %, relative to the total extractant. It is more preferable for the extractant simultaneously contains both at least 20 wt. %, relative to the total extractant, of an alcohol (preferably ethanol) and water in a proportion of at least 15 wt. %, relative to the total extractant.

Blackberry leaf extracts that are particularly effective in the compositions and methods of this invention are obtained with an extract containing ethanol and water in the ratio of about 2:8 (2 parts by weight of ethanol mixed with 8 parts by weight of water) to about 8:2, more preferably in the ratio of about 3:7 to about 7:3 and most preferably in the ratio of about 3:7 to about 1:1.

Accordingly, in one preferred embodiment, the blackberry extract is a blackberry leaf extract, i.e., the extract is produced from the leaves of the blackberry plant. In a particularly preferred embodiment, the blackberry extract is produced from the leaves of *Rubus fruticosus*. In a further particularly preferred embodiment, the blackberry extract is produced by extracting the leaves of *Rubus fruticosus* with a mixture of water and a lower alcohol such as ethanol as set forth above.

One particularly suitable blackberry extract is produced by extracting the leaves of *Rubus fruticosus* with a mixture of water and ethanol is commercially available as compounded to an activity of about 5% to about 10%, with a maltodextrin matrix, from Symrise Inc. of Teterboro, N.J., and is sold under the name, "SymMatrix."

Detailed procedures for preparing a suitable blackberry leaf extract are set forth in U.S. Patent Publication No. 2008/0095719, which is herein incorporated in its entirety.

As used herein, "topical application" means directly laying on or spreading on outer skin using, e.g., by use of the hands or an applicator such as a wipe, puff, roller, or spray.

As used herein, "cosmetically-acceptable" means that the product(s) or compound(s) which the term describes are suitable for use in contact with tissues (e.g., the skin) without undue toxicity, incompatibility, instability, irritation, allergic response, and the like. This term is not intended to limit the ingredient/product, which it describes to use solely as a cosmetic (e.g., the ingredient/product may be used as a pharmaceutical).

As used herein, "topical carrier" means one or more compatible solid or liquid filler diluents that are suitable for topical administration to a mammal. Examples of topical carriers include, but are not limited to, water, waxes, oils, emollients, emulsifiers, thickening agents, gelling agents, and mixtures thereof.

As used herein, "hair" means scalp, head, facial and/or body hair, including but not limited to the scalp, eye lashes, brows, mustache, beard, ear, nasal, chest, pubic, auxiliary and the like.

As used herein, "inducing hair growth" means the earlier induction of growth of a new hair cycle, and/or prolonging the active growth phase (anagen) of the hair cycle and/or increasing the growth rate of the hair and/or increasing the width of hair shaft, including, but not limited to, the induction of the growth of hair and making it more visible to the eye.

As used herein, "improving hair quality" means increasing the diameter of the hair shaft and/or enhancing the visual attributes of the hair like hair volume, hair shine and hair thickness, and/or affecting the characteristics of the hair shaft and/or hair cuticles, including, but not limited to, creating a smoother look or feel, and/or increase in shine.

As used herein, "safe and effective amount" means an amount of a physiologically active compound or composition sufficient to induce a positive modification in the condition to be regulated or treated, (e.g. hair growth) but low enough to avoid serious side effects. The safe and effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

Topical Compositions

The topical compositions useful in this invention contain formulations suitable for topical application to the hair and scalp. In one embodiment, the composition contains a blackberry extract and a cosmetically-acceptable topical carrier. In one embodiment, the cosmetically-acceptable topical carrier constitutes from about 75% to about 95%, by weight, of the composition more preferably from about 75% to about 85%, by weight, of the composition.

The compositions of this invention may be made into a wide variety of product types that include but are not limited to solid and liquid compositions such as lotions, creams, gels, sticks, sprays, ointments, cleansing liquid washes and solid bars, shampoos, pastes, powders, foams, mousses, and wipes. These product types may contain several types of cosmetically acceptable topical carriers including, but not limited to solutions, emulsions (e.g., microemulsions and nanoemulsions), gels, solids and liposomes. Non-limiting examples of such carriers are set forth herein. Other carriers may be formulated by those of ordinary skill in the art.

The topical compositions useful in the present invention can be formulated as solutions. Solutions should preferably include an aqueous solvent (e.g., from about 75% to about 95% or from about 75% to about 85% of a cosmetically acceptable aqueous solvent). More preferably, such compositions should contain about 30% solvent, although this may vary dependent upon the formulation. Such solvents may include ethanol, propylene glycol, polyethylene glycol, mixtures thereof and the like which are good carriers for successful delivery to the hair follicles.

Topical compositions useful in the subject invention may be formulated as a solution containing an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. The International Cosmetic Ingredient Dictionary and Handbook, Fourteenth Edition, 1012 Volume 3, eds. Gottschlack and Breslawec, pp. 3868-80, published by Personal Care Products Council (hereinafter, "INCI Handbook"), which is hereby incorporated herein by reference.

A lotion may be made from a solution. Lotions typically contain from about 1% to about 20% (more preferably, from about 5% to about 10%) of an emollient(s) and from about 50% to about 90% (more preferably, from about 60% to about 80%) of water.

Another type of product may be a solution that is a cream. A cream typically comprises from about 5% to about 50% (more preferably, from about 10% to about 20%) of an emollient(s) and from about 45% to about 85% (more preferably, from about 50% to about 75%) of water.

Yet another type of product that may be formulated from a solution is an ointment. An ointment may be constituted of a simple base of animal or vegetable oils or semi-solid hydrocarbons. An ointment may contain from about 2% to about 100% of an emollient(s), and from about 0.1% to about 2% of a thickening agent(s). The INCI Handbook contains a list of acceptable thickening agents or viscosity increasing agents useful in the compositions and methods of this invention at pages 1693 through 1697.

The topical compositions useful in the present invention may also be preferably formulated as emulsions. If the carrier is an emulsion, from about 1% to about 10% (preferably from about 2% to about 5%) of the carrier should be made up one or more emulsifiers. Emulsifiers may be nonionic, anionic or cationic. Suitable emulsifiers may be found in, for example, the INCI Handbook, pp. 3816-191 and 3954-67.

Lotions and creams may also be formulated as emulsions. Typically such lotions preferably contain from 0.5% to about 5% of an emulsifier(s). Such creams would typically comprise from about 1% to about 20% (preferably from about 5% to about 10%) of an emollient(s); from about 20% to about 80% (preferably, from 30% to about 70%) of water; and from about 1% to about 10% (preferably, from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

Compositions of this invention may also be in the form of shampoo, hair conditioning products, leave-on hair masks, mousse, sprays, in combination with dyes and other hair care products for cleaning, treating, conditioning and coloring the hair simultaneous with topical application of the novel compositions of this invention.

The topical compositions of this invention may be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents. Microgels may be used to enhance follicular delivery of the formulations.

The topical compositions of this invention may also be formulated into a solid formulation (e.g., a wax-based stick, mascara, soap bar composition, powder, or a wipe containing powder.

The topical compositions useful in this invention may contain, in addition to the aforementioned components, a wide variety of additional oil-soluble, organic solvent-soluble, and/or water-soluble materials conventionally used in compositions for use on skin and hair, at their art-established levels. For example, a formulation of 70% ethanol and 30% propylene glycol or variable amounts of these two agents may be used for enhanced delivery of the actives.

Surfactants

In one embodiment, the composition of this invention contains one or more surfactants. In one embodiment, the composition contains a lathering surfactant. What is meant by a "lathering surfactant" is a surfactant that generates lather when combined with water and mechanically agitated. In one embodiment, the lathering surfactant has an initial foam height reading of at least 20 mm, such as at least 50 mm, in the Standard Test Method for Foaming Properties of Surface-Active Agents D1173-53 Set forth in the ASTM Annual Book of ASTM Standards 1001 Section 15 Volume 15.04 (using a concentration of 5 grams per liter, temperature of 49° C., and water hardness of 8 grains per gallon). Examples of lathering surfactants include, but are not limited to, anionic, nonionic, cationic, and amphoteric lathering surfactants.

Non-limiting examples of anionic lathering surfactants include those selected from the group consisting of sarcosinates, sulfates, isethionates, taurates, phosphates, lactylates, and glutamates. Specific examples include, but are not limited to, those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Non-limiting examples of nonionic lathering surfactants include those selected from the group consisting of alkyl glucosides, alkyl polyglucosides, polyhydroxy fatty acid amides, alkoxylated fatty acid esters, lathering sucrose esters, amine oxides, and mixtures thereof. Specific examples include, but are not limited to, nonionic surfactants to those selected form the group consisting of C8-C14 glucose amides, C8-C14 alkyl polyglucosides, sucrose cocoate, sucrose laurate, lauramine oxide, cocoamine oxide, and mixtures thereof.

Non-limiting examples of amphoteric lathering surfactants (which also includes zwitterionic lathering surfactants are those selected from the group consisting of betaines, sultaines, hydroxysultaines, alkyliminoacetates, iminodialkanoates, aminoalkanoates, and mixtures thereof.

Non-limiting examples of amphoteric surfactants of the present invention include disodium lauroamphodiacetate, sodium lauroamphoacetate, cetyl dimethyl betaine, cocoamidopropyl betaine, cocoamidopropyl hydroxy sultaine, and mixtures thereof.

Additional Cosmetically Active Agents

In one embodiment, the compositions according to this invention may further contain one or more additional cosmetically active agent(s) as well as the above-mentioned components. What is meant by a "cosmetically active agent" is a compound, which may be a synthetic compound or a compound isolated, purified or concentrated from a natural source, or a natural extract containing a mixture of compounds, that has a cosmetic or therapeutic effect on the tissue, including, but not limited to: anti-microbial agents such as anti-yeast agents, anti-fungal, and anti-bacterial agents, anti-inflammatory agents, anti-aging agents, anti-parasite agents, external analgesics, sunscreens, photoprotectors, antioxidants, keratolytic agents, detergents/surfactants, moisturizers, nutrients, vitamins, minerals, energy enhancers, antiperspiration agents, astringents, hair growth enhancing agents, hair coloring agents, pigments, firming agents, agents for skin conditioning, and odor-control agents such as odor masking or pH-changing agents.

In one embodiment, the cosmetically active agent may be selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids such as retinoic acid (tretinoin) and retinoid precursors such as retinol and retinyl palmitate, vitamins such as vitamin E (alpha, beta or delta tocopherols and/or their mixtures) ceramides, polyunsaturated fatty acids, essential fatty acids, enzymes, enzyme inhibitors, minerals, hormones such as progesterones, steroids such as hydrocortisone, 2-dimethylaminoethanol, metal (including but not limited to iron or zinc) salts such as copper chloride, peptides containing copper such as Cu:Gly-His-Lys, coenzyme Q10, amino acids, vitamins, acetyl-coenzyme A, niacin, riboflavin, thiamin, ribose, electron transporters such as NADH and FADH2, botanical extracts such as aloe vera, feverfew, and soy, and derivatives and mixtures thereof. The cosmetically active agent will preferably be present in the composition of the invention in an amount of from about 0.001% to about 20% by weight of the composition, more preferably, from about 0.005% to about 10% and most preferably, from about 0.01% to about 5%.

Also expected to be particularly effective in the compositions and methods of this invention are the presence of synthetic or natural 5-alpha reductase inhibitors, or other anti-sebum ingredients including, but not limited to, Sepicontrol (Capryloyl Glycine, Sarcosine and Cinamomum Zeylanicum Bark Extract), licorice powder or extract, and the like. MC5 receptor antagonists may also be utilized in the compositions of this invention. Examples of MC5-R antagonists may be found in U.S. Pat. No. 7,049,331.

The compositions of this invention may also be utilized in combination with compounds known to promote hair growth that are available as drugs, such as finasteride (Propecia), a type 2 5-alpha-reductase inhibitor, and dutasteride, a type 1- and 2-5-alpha-reductase inhibitor, as well as flutamide, bicalutamide, pregnane derivatives, progesterone derivatives, experimental agents such as FCE 28260 and the like. Spironolactone and other diuretics may also be utilized as it is indicated for women in some cases (also known as Aldactone: an aldosterone receptor antagonist). Potassium channel openers, such as Minoxidil (Rogaine), which are known to promote hair growth, are also believed to be especially promising combinations.

Herbal remedies that may have 5-alpha reductase inhibitory action may include: Saw Palmetto and Pygeum africanum. Other agents that may have such activity are Beta-sisterol, Sepicontrol and Licorice, gamma-linolenic acid and other unsaturated fatty acids (Tehming LIANG and Shutsung LIAO) Biochem. J. (1992) 285, 557-562, Inhibition of steroid 5-alpha-reductase by specific aliphatic unsaturated fatty acids), Zinc and Zinc salts, green tea catechin (−)-epigallocatechin gallate (EGCG) and other polyphenols, and the like. Grape seed, apple seed, apple juice and barley extracts may also be potential agents that may induce hair growth, although they are not thought to be very common(s) or satisfactory in achieving satisfactory results (Takahashi et al., Procyanidin Oligomers Selectively and Intensively Promote Proliferation of Mouse Hair Epithelial Cells In Vitro and Activate Hair Follicle Growth In Vivo, J Invest Dermatol 112:310-316).

Additional combinations may include other known stimulators of hair growth, such as, zinc, calcineurin inhibitors such as FK506 (Tacrolimus, Fujimycin), a macrolide antibiotic produced by *Streptomyces tsukubaensis*, and its derivatives, or Cyclosporin A, a cyclic endecapeptide and a T cell-specific immunosuppressant, and the like.

Active ingredients in Provillus, a product suggested to block DHT (Vitamin B6, Biotin, Magnesium, Zinc, Saw Palmetto, Nettle, Gotu Kola, Pumpkin, Eleuthero Root, Uva-Ursi, Muria Puama) may also be included in the compositions of this invention.

Examples of vitamins that may be constituents of the compositions of this invention include, but are not limited to, vitamin A, vitamin Bs such as vitamin B3, vitamin B5, and vitamin B12, vitamin C, vitamin K, vitamin E such as alpha, gamma or delta-tocopherol, and derivatives (such as salts and esters) and mixtures thereof.

Examples of hydroxy acids include, but are not limited, to glycolic acid, lactic acid, malic acid, salicylic acid, citric acid, and tartaric acid. Such hydroxy acids, it is believed, serve to support the regeneration of the corneous layer of the scalp. We also believe that such hydroxy acids assist in normalizing the pH of the compositions of this invention and may, as with lactic acid, add a conditioning effect to the hair.

Examples of antioxidants which may be utilized in the compositions and methods of this invention include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention, include, but not limited to, extracts containing flavonoids, isoflavonoids, and their derivatives such as genistein and daidzein (e.g., such as soy and clover extracts, extracts containing resveratrol and the like. Examples of such natural extracts include grape seed, green tea, pine bark, and propolis.

Progesterones, and naturally-derived ingredients with progesterone-like activity, on the other hand, may be useful, as well as astringents such as witch hazel, triclosan, cerulenin, alpha-methylene-gamma-butyralactone, glycine derivatives such as capryloylglycine and methylglycine, salicylic acid, or benzoyl peroxide.

Fabao 101, which has the following active ingredients, may also be included in the compositions of this invention: *Aralia Quinquetolia, Astragalus Glycyphyllos, Angelica Arhangelica* Root, *Salvia Officinalis, Capsicum, Carya Alba, Corthamis Tinctorius,* Cortex dictamni radicis, Flos Chrysanthemum, Heshouwu, Iron-Fist Ginseng, Miltiorrhizae, *Notoginseng,* Paorulca Glandulosa, Peach Kernel Oil, Rhizome of Szechuan Lovage, Radix astragali, Radix Ginseng, Radix Polygoni Multiflori, Red-rooted Salvia, Rhizhoma gastroidia ginseng, Seu radix notopterygii, *Sophera flavescens.*

Other Materials

Various other materials may also be present in the compositions useful in the subject invention. These include humectants, proteins and polypeptides, preservatives and an alkaline agent. Examples of such agents are disclosed in the INCI Handbook, pp. 1650-1667. The compositions of the present invention may also comprise chelating agents (e.g., EDTA) and preservatives (e.g., parabens). Examples of suitable preservatives and chelating agents are listed in pp. 1626 and 1654-55 of the INCI Handbook. In addition, the topical compositions useful herein can contain conventional cosmetic adjuvants, such as dyes, opacifiers (e.g., titanium dioxide), pigments, and fragrances.

Darkening Agents

In one embodiment, the compositions of the present invention further contain darkening agents such as melanin or synthetic melanin derivatives, or melanin-like molecules, vanillin polymers, natural extracts such as, but not limited to Coleus Forskoli extract, Bugrane-P extract, extracts from natural sources containing pigments (e.g., brown pigments from plants from the *Hedychium* genus or *Bearberry* genus or yellow, orange and red pigments, from plants containing carotenoids or canthaxanthins); or synthetic chemicals such as compounds containing copper (e.g., copper salts such as $CuCl_2$) or synthetic carotenoids or canthaxantins. Examples of synthetic melanin derivatives are set forth in U.S. Pat. Nos. 5,618,519, 5,384,116, and 5,227,459. Examples of soluble melanin derivatives are set forth in U.S. Pat. Nos. 5,744,125, 5,225,435, 5,218,079, and 5,216,116. Examples of commercially available soluble melanin derivatives include Melasyn-100™ from San-mar laboratories, Inc. (Elmsford, N.Y.) and MelanZe™ from Zylepsis (Ashford, Kent, United Kingdom).

These agents will preferably be present in the composition in an amount from about 0.001% to about 10% by weight, in particular in an amount from about 0.01% to about 5% by weight.

In another embodiment, the composition may include a peptide. Examples of darkening peptides are set forth in U.S. Pat. No. 7,025,951. The peptide of the invention set forth therein may be provided in the form of cosmetically acceptable salts. Examples of preferred salts are those with therapeutically acceptable organic acids, e.g., acetic, palmitic, oleic, stearic, lactic, maleic, citric, malic, ascorbic, succinic, benzoic, salicylic, methanesulfonic, or Palmoic acid, as well as polymeric acids such as tannic acid or carboxymethyl cellulose, and salts with inorganic acids such as the hydrohalic acids (e.g., hydrochloric acid), sulfuric acid or phosphoric acid.

The amount of peptide present in the composition depends on the peptide used. The peptide should be present in the composition in an amount from about 0.001% to about 10% by weight, in particular in an amount from about 0.005% to about 5% by weight.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water comprises at least about 10 mg/L of calcium and/or at least about 5 mg/L of magnesium.

Methods of Use

The compositions of this invention may be utilized to induce hair growth by topical application of said compositions to the area of the body on which hair growth is desired. Preferably, the compositions of this invention are applied topically to the desired area of the body at least once per day for at least five (5) days and more preferably on a daily basis for at least six weeks and most preferably, indefinitely. For improvement to hair quality, said compositions should be applied at least once per day for at least twelve weeks. After about two weeks, the user may begin to observe increased hair growth and may be able to observe increased hair shaft diameter and/or enhanced visual attributes of the hair, such as hair volume, hair shine and hair thickness.

EXAMPLES

Example 1

A gel base formula A1 was prepared according to Table 1 below:

The following ingredients were combined in a mixing vessel: DI water, Disodium EDTA, Glycerin, Dimethicone and Butylated Hydroxytoluene (BHT) and heated to 40-45° C. while using prop mixing at medium to high speed (sweep blade) and mixed until uniform. Once a temperature below 40° C. was achieved the following ingredients were added one at a time with prop mixing (sweep blade, medium speed): Sepigel 305, Phenonip XB. The pH was adjusted to 5.0 with Sodium Hydroxide.

TABLE 1

| INCI Name | gms |
|---|---|
| Water | 364.5 |
| Disodium EDTA | 10.00 |
| Glycerin | 30.00 |
| Dimethicone | 20.00 |
| Butylated Hydroxytoluene | 0.50 |
| Polyacrylamide & Laureth 7 & C13 - 14 Isoparafin | 65.00 |
| Phenoxyethanol & Methylparaben & Propylparaben & Ethylparaben | 10.00 |
| NaOH, 20% w/w in water | Qs |

Example 2

A composition containing blackberry extract (A2) and a composition containing only butylene glycol and water (A3) were prepared in accordance with the procedure set forth in Example 1 with the following formulas set forth in Table 2.

TABLE 2

| INCI Name | A2 % w/w | A3 % w/w |
|---|---|---|
| *Rubus fruticosus* | 50.00 | 0.00 |
| Butylene Glycol | 25.00 | 25.00 |
| Water | 25.00 | 75.00 |
| Total | 100 | 100.00 |

Example 3

Compositions E1 and C were prepared according to the following formula in Table 3. Inventive example E1 was prepared by combining the gel base A1 of Example 1 and the Blackberry extract composition A2 of Example 2 to yield a concentration of 25% blackberry extract (a 1:1 ratio of A1 and A2) by mixing until uniformity was achieved. Additionally, comparative example C1 was prepared by combining gel base A1 and A3 of Example 2.

Example 4

Hair Growth Induction in C3H Mice with Blackberry (*Rubus fruticosus*) Extract Hair growth induction in C3H mice was measured as a percentage of mice entering the anagen phase as a function of time (days of study).

C3H female mice age 6-7 weeks was purchased from Taconic Farms (Germantown, N.Y.). Mice were housed in appropriately sized cages in an environmentally controlled room with a 12-hour light-12-hour dark photoperiod and supplied with food and water ad libitum. Animal care was based on the "Guide for the Care and Use of Laboratory Animals", NIH Publication No. 85-23. Animals were acclimated for a week before study starts. Once all mice have entered their prolonged telogen/resting phase (about 50-60 days long) of the hair cycle, they were clipped over the dorsal area about 1.5×5 cm (Wahl Clippers 8900 Series, Blade # 1086). Four female mice per group were clipped while sedated with 2% induction and maintenance isoflurane and 0.5L Oxygen. In addition to E1 (250 mg/ml *Rubus fruticosus* formulation), the treatment groups included a placebo (C1) and an untreated group (n=4) to serve as control for natural hair growth initiation and to observe placebo effects and 200 µl of test materials were applied topically to the area daily, five days a week (Monday through Friday). Images were taken at the first signs of anagen/active growth phase and when needed based on visual observation. A study log documenting day-to-day observations of mice entering anagen (grey skin) was recorded. Treatments continued for up to about 8 weeks.

TABLE 4

HAIR GROWTH INDUCTION IN C3H MICE REPRESENTING % OF MICE ENTERING ANAGEN AS A FUNCTION OF TIME (DAYS OF STUDY)

| | Groups/Day % mice entering anagen | | | | | | | | | | | | | | | | | |
|---|---|---|---|---|---|---|---|---|---|---|---|---|---|---|---|---|---|---|
| | 7 | 8 | 9 | 10 | 14 | 20 | 22 | 23 | 24 | 29 | 31 | 35 | 42 | 43 | 44 | 45 | 46 | 50 |
| Untreated (n = 4 animals) | 0 | 0 | 0 | 0 | 0 | 0 | 0 | 0 | 0 | 0 | 0 | 0 | 0 | 0 | 0 | 0 | 0 | 0 |
| 25% Symmatrix (n = 4 animals) (E1) | 50 | 100 | 100 | 100 | 100 | 100 | 100 | 100 | 100 | 100 | 100 | 100 | 100 | 100 | 100 | 100 | 100 | 100 |
| Symmatrix Placebo (n = 4 animals) (C1) | 0 | 0 | 0 | 0 | 0 | 0 | 0 | 0 | 0 | 0 | 0 | 0 | 0 | 25 | 50 | 50 | 75 | 100 |
| Most effective of 5% Minoxidil (N = 4 studies) | 0 | 0 | 20 | 40 | 80 | 80 | 80 | 80 | 75 | 100 | 100 | 100 | 100 | 100 | 100 | NA | NA | NA |
| Average 5% Minoxidil (N = 4 studies) | 0 | 0 | 7 | 18 | 31 | 32 | 41 | 38 | 36 | 36 | 45 | 48 | 63 | 87 | 93 | NA | NA | NA |

Number of animals per group for Minoxidil reference: Day 7-22 (N = 7), Day 23-26 (N = 6), Day 27-44 (N = 5)
NA = Not Assessed

TABLE 3

| | E1 % w/w | C1 % w/w |
|---|---|---|
| A1 | 50.00 | 50.00 |
| A2 | 50.00 | 0 |
| A3 | 0.00 | 50.00 |
| Total | 100.00 | 100.00 |

Surprisingly the *Rubus fruticosus* topical treatment (E1) induced hair growth in all the C3H mice by day 8. When evaluations are compared against a commercially available hair growth product (5% Generic Minoxidil Solution for Men purchased from Eckerd Pharmacy) using the same test model, the induction with E1 topical application occurred faster and at a higher incidence/responder rate. On average about 63% of mice treated with 5% marketed Minoxidil entered anagen by week 6 (N=4 studies) with 100% by week 4 (Day 29) where Minoxidil performed the best as a positive control.

Hence, we conclude that the hair growth induction occurred faster and at a higher incidence when treated with E1 resulting in a 100% responder rate at eight (8) days compared with 5% marketed Minoxidil where on average about 63% of mice (n=4 studies) entered anagen by week 6 and with 100% by week 4 (Day 29) where Minoxidil performed the best as a positive control.

Example 5

Medium consisting of Williams E medium (minus glutamine), L-glutamine, Fungizone, penicillin and streptomycin (supplied by Gibco) was prepared. A stock solution of Blackberry extract and medium was prepared. 1:10 serial dilutions of the stock solution were prepared until the appropriate concentration was achieved.

Human terminal hair follicles are isolated from fresh facial cosmetic surgery samples. Individual follicles are placed into 12 well Falcon insert cell culture plates in a 0.4 um insert filled with 0.5 ml of medium. Treatments are added to the medium using a w/v calculation. Medium is changed every other day. Images are taken on Day 0, 1, 3, 5, 7 & 9. Image analysis is done by measuring the length of the hair shaft. Means of each group and percent increases are calculated.

TABLE 5

| Treatment | N | % change over untreated |
|---|---|---|
| Untreated | 9 | 0 |
| Blackberry Ext. 0.01% | 10 | −4.278326281 |
| Blackberry Ext. 0.001% | 7 | 63.6577339 |

Blackberry extract (*Rubes fruticosus*) at 0.001% (w/v) was able to increase hair shaft elongation by 63.65% compared to follicles grown medium without the blackberry extract.

Example 6

Human hair follicles were isolated from fresh facial cosmetic surgery samples. Individual follicles were placed into 6 well Falcon insert cell culture plates onto 0.4 μm inserts filled with 2.0 mL of medium. The medium and a stock solution as in Example 5 were prepared. Treatments were added to the medium using a w/v calculation. Medium was changed every other day. Images were taken on Day 0, 1, 3, 5, 7, and 9. Image analysis was done by measuring the length of the hair shaft. Means of each group and percent increases were calculated.

TABLE 6

| Treatment | N | % Change over untreated |
|---|---|---|
| Untreated | 12 | 0 |
| Blackberry Ext. 0.001% | 5 | 51.936 |
| Blackberry Ext. 0.001% | 4 | 44.412 |
| Blackberry Ext. 0.0001% | 4 | 15.466 |
| Blackberry Ext. 0.05% | 5 | −27.4437 |

Blackberry extract (*Rubes fruticosus*) at concentration ranges between 0.0001% to 0.001% (w/v) was able to increase hair shaft elongation by more than 15% compared to follicles grown medium without the blackberry extract. It should be noted that, unexpectedly, blackberry extract at the higher concentration range of 0.05% did not increase hair shaft elongation.

Example 7

The following embodiments were made using the formulations set forth in Table 7:

| INCI Name | C2 | C3 | C4 | C5 | C6 | C7 | C8 | C9 | E2 | E3 | E4 | E5 |
|---|---|---|---|---|---|---|---|---|---|---|---|---|
| Water DI | 88.97 | 88.97 | 64.97 | 64.67 | 63.47 | 75.97 | 73.97 | 73.97 | 79.47 | 79.17 | 60.3 | 69.8 |
| Carbomer-Acrylic Acid, Cyclohexane | | | 0.5 | 0.8 | | | | | 1 | 1.5 | 2 | 2.5 |
| Sodium Polyacrylate (and) Hydrogenated Polydecene | | | | | 2 | | | | | | | |
| Methulcellulose and Hydroxypropyl Methylcellulose | | | | | | 5 | | | | | | |
| Lithium Magnesium Sodium Silicate | | | | | | | 2 | 3 | 4 | | | |
| Dehydroxanthan Gum | 0.5 | | | | | 0.5 | 0.5 | 0.5 | | | | |
| Butylene Glycol | | | | | | 2 | 2 | 2 | | | | |
| Sodium Hydroxide 20% Soln. | q.s. | q.s. | q.s. | q.s. | q.s. | q.s. | q.s. | q.s. | q.s. | q.s. | q.s. | q.s. |
| Glycerin | 1 | | | | | | | | | | | |
| Glyceryl Polymethacrylate | | | 24 | 24 | 24 | 10 | 10 | 10 | 10 | 10 | 20 | 10 |
| Maltodextrin (40%) *Rubus Fruticosus* (Blackberry) Leaf Extract (60%) | 8.33 | 8.33 | 8.33 | 8.33 | 8.33 | 8.33 | 8.33 | 8.33 | 8.33 | 8.33 | 16.7 | 16.7 |
| Phenoxyethenol | 0.7 | 0.7 | 0.7 | 0.7 | 0.7 | 0.7 | 0.7 | 0.7 | 0.7 | | | |
| Sodium Benzoate | 0.5 | 0.5 | 0.5 | 0.5 | 0.5 | 0.5 | 0.5 | 0.5 | 0.5 | | | |
| Phenoxyethenol (and) Caprylyl Glycol (and) Sorbic Acid | | | | | | | | | | 1 | 1 | 1 |
| Polyacrylamide (and) C13-14 Isoparaffin (and) Laureth- 7 | | | 1 | 1 | 1 | | | | | | | |
| Result | 100 Too thin | 100 too thin | 100 did not thicken | 100 insufficiently thick o form gel | 100 pancake mix with clumps | 100 thin | 100 paste | 100 thick grit | 100 GEL | 100 Stable Gel | 100 Thin Gel | 100 Gel |

Each of the embodiment compositions set forth in Table 7 was independently prepared as follows:

E2-E5:

Water was measured into a main vessel and stirring with vortex initiated. Carbomer-Acrylic Acid, Cyclohexane was slowly added by screen sifting. The mixture was heated until the temperature reached 55-60° C. A 20% Sodium Hydroxide solution was made. The pH was adjusted with a 20% Solution Sodium Hydroxide to pH 5.5-6 to neutralize the Carbomer. The heat was turned off and the mixture was cooled down to 45° C. The Maltodextrin (40%) *Rubus Fruticosus* (Blackberry) Leaf Extract (60%) was premixed in Glyceryl Polymethacrylate. The Maltodextrin (40%) *Rubus Fruticosus* (Blackberry) Leaf Extract (60%), Glyceryl Polymethacrylate paste was added to the vessel with stirring. The viscosity continued to decrease as it was added. The pH was adjusted with a 20% solution of Sodium Hydroxide to pH 5.5-6.0. The Phenoxyethanol (and) Caprylyl Glycol (and) Sorbic Acid were added to the beaker (Formulation C12 had Phenoxyethanol and Sodium Benzoate) with stirring. The pH was adjusted with a 20% Solution of Sodium Hydroxide to pH 5.5-6. QS with Water was performed. A gel was formed.

E-2—A stable gel was formed and the formula passed 13 weeks stability. Stability was tested using a T spindle at 20 RPM for two weeks and four weeks. The samples were kept at room temperature, 4° C., 40° C. and 50° C. The sample kept at 50° C. was taken out of the test at six weeks and the other samples (room temperature, 4° C. and 40° C.) were read at eight weeks and 13 weeks. A freeze/thaw test was performed on three cycles. As more (40%) *Rubus Fruticosus* (Blackberry) Leaf Extract (60%) is added, more Carbomer must be added.

C2—For C2, the same procedure was followed with the exception that Dehydroxanthan Gum was pre-wet with glycerin and slowly added to the vessel with stirring. The Maltodextrin (40%) *Rubus Fruticosus* (Blackberry) Leaf Extract (60%) was not pre-wet with Glyceryl Polymethacrylate. The preservative added was Phenoxyethanol and Sodium Benzoate.

C3—For C3 the same procedure was followed with the exception of after the water was added to the vessel, it was heated until the temperature reached 55-60° C. Methylcellulose and Hydroxy Propyl Methylcellulose were slowly added with stirring for 30 minutes. The Maltodextrin (40%) *Rubus Fruticosus* (Blackberry) Leaf Extract (60%) was not pre-wet with Glyceryl Polymethacrylate. It was sprinkled in directly to the vessel.

C4 and C5—For C4 and C5, the same procedure was followed with the exception that Polyacrylamide (and) C13-14 Isoparaffin (and) Laureth-7 was post added to the composition.

C6—For C6, the same procedure was followed with the exception that Sodium Polyacrylate (and) Hydrogenated Polydecene was sprinkled in the water. Polyacrylamide (and) C13-14 Isoparaffin (and) Laureth-7 was post added to the formula.

C7, C8 and C9—For C7, C8 and C9, the same procedure was followed with the addition of Dehydroxanthan Gum pre-wet in Butylene Glycol. Continued mixing and slowly added Lithium Magnesium Sodium Silicate. It was noted that as more Laponite was added to the composition, the consistency became more of a paste as opposed to becoming a gel).

What is claimed is:

1. A method of increasing hair growth in a human in need thereof comprising topically administering to the scalp, the skin, the eyelashes, the eyebrows, the mustache region or the beard region of the human in need thereof a topically active composition comprising a concentration of at least 90 mg extract/ml of solution but less than 300 mg extract/ml of solution of a Rubus fruticosus extract, which increases the amount of hair on the scalp, the skin, the eyelashes, the eyebrows, the mustache region or the beard region of the human after daily application of the topically active composition for at least seven days.

2. The method of claim 1, wherein said topically active composition comprises a concentration of at least 120 mg of extract/ml of solution but less than 300 mg of extract/ml of solution of a Rubus fruticosus extract.

3. The method of claim 1, wherein said topically active composition comprises a concentration of at least 250 mg of extract/ml of solution but less than 300 mg of extract/ml of solution of a Rubus fruticosus extract.

* * * * *